US00PP16927P2

(12) United States Plant Patent
Oudshoorn

(10) Patent No.: US PP16,927 P2
(45) Date of Patent: Aug. 1, 2006

(54) ***SEDUM* PLANT NAMED 'SUNKISSED'**

(50) Latin Name: *Sedum telephium*
Varietal Denomination: Sunkissed

(75) Inventor: Hubertus Gerardus Oudshoorn, Rijpwetering (NL)

(73) Assignee: Future Plants Licentie B.V., Lisserbroek (NL)

( * ) Notice: Subject to any disclaimer, the term of this patent is extended or adjusted under 35 U.S.C. 154(b) by 0 days.

(21) Appl. No.: 11/141,610

(22) Filed: May 31, 2005

(51) Int. Cl.
*A01H 5/00* (2006.01)

(52) U.S. Cl. ..... Plt./263
(58) Field of Classification Search ..... Plt./263
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Sedum* plant named 'Sunkissed', characterized by its upright and compact plant habit; freely basal branching growth habit; relatively short peduncles; and yellow-colored flowers.

2 Drawing Sheets

Botanical designation: *Sedum telephium.*
Cultivar denomination: 'Sunkissed'.

BACKGROUND OF THE INVENTION

The present Invention relates to a new and distinct cultivar of *Sedum* plant, botanically known as *Sedum telephium,* and hereinafter referred to by the name 'Sunkissed'.

The new *Sedum* is a product of a planned breeding program conducted by the Inventor in Rijpwetering, The Netherlands. The objective of the breeding program is to develop new compact *Sedum* cultivars with uniform growth habit and attractive flower coloration.

The new *Sedum* originated from a chance cross-pollination made by the Inventor in 2001 of two unknown seedling selections of *Sedum telephium.* The new *Sedum* was discovered and selected by the Inventor as a single flowering plant within the progeny of the stated chance cross-pollination grown in a controlled environment in Rijpwetering, The Netherlands in 2002.

Asexual reproduction of the new cultivar by terminal cuttings taken at Rijpwetering, The Netherlands, since 2003, has shown that the unique features of this new *Sedum* are stable and reproduced true to type in successive generations.

SUMMARY OF THE INVENTION

Plants of the cultivar Sunkissed have not been observed under all possible environmental conditions. The phenotype may vary somewhat with variations in environment such as temperature and light intensity without, however, any variance in genotype.

The following traits have been repeatedly observed and are determined to be the unique characteristics of 'Sunkissed'. These characteristics in combination distinguish 'Sunkissed' as a new and distinct cultivar:

1. Upright and compact plant habit.
2. Freely basal branching growth habit.
3. Relatively short peduncles.
4. Yellow-colored flowers.

Plants of the new *Sedum* can also be compared to plants of the *Sedum telephinum* cultivar Cream Explanation, not patented. In side-by-side comparisons conducted in Rijpwetering, The Netherlands, plants of the new *Sedum* differed from plants of the cultivar Cream Explanation in the following characteristics:

1. Plants of the new *Sedum* were more compact than plants of the cultivar Cream Explanation.
2. Plants of the new *Sedum* and the cultivar Cream Explanation differed in flower coloration as plants of the cultivar Cream Explanation had cream-colored flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Sedum.*

The photograph on the first sheet comprises a side perspective view of a typical flowering plant of 'Picolette' grown in a container.

The photograph at the top of the second sheet comprises a close-up view of a typical inflorescence of 'Picolette'.

The photograph at the bottom of the sheet is a close-up view of the upper surface of a typical leaf of 'Picolette'.

DETAILED BOTANICAL DESCRIPTION

In the following description, color references are made to The Royal Horticultural Society Colour Chart, 2001 Edition, except where general terms of ordinary dictionary significance are used. Plants used for the aforementioned photographs and following description were grown under conditions which closely approximate commercial production conditions during the late summer in an outdoor nursery in Rijpwetering, The Netherlands for about one year. During the production of the plants, day temperatures ranged from 14 to 32° C. and night temperatures ranged from 7 to 18° C.

Botanical classification: *Sedum telephium* cultivar Sunkissed.

Parentage:

*Female parent.*—Unknown seedling selection of *Sedum telephium,* not patented.

*Male parent.*—Unknown seedling selection of *Sedum telephium,* not patented.

Propagation:

*Type cutting.*—Terminal vegetative cuttings.

*Time to produce a rooted young plant.*—About three months at 18° C.

*Root description.*—Thick, fleshy; light brown in color.

*Rooting habit.*—Freely branching.

Plant description:

*Form/growth habit.*—Upright and compact plant form; inverted triangle. Freely basal branching, about three basal branches per plant; moderately vigorous growth habit. Numerous single flowers arranged in terminal and axillary cymes.

*Plant height.*—About 21 cm.

*Plant width.*—About 21.5 cm.

*Branch description.*—Length: About 6.7 cm. Diameter: About 5.5 mm. Internode length: About 4.3 cm. Strength: Moderately strong. Aspect: Mostly upright. Texture: Smooth, glabrous; succulent. Color: 144B to 144C.

*Foliage description.*—Arrangement: Opposite, simple; sessile. Length: About 5.9 cm. Width: About 3.9 cm. Shape: Broadly ovate. Apex: Bluntly acute. Base: Cordate to cuneate; clasping. Margin: Irregularly serrate. Texture, upper and lower surfaces: Smooth, glabrous; succulent. Venation pattern: Pinnate; arcuate. Color: Developing foliage, upper surface: 144A to 144B. Developing foliage, lower surface: 143B to 143C. Fully expanded foliage, upper surface: Between 143A and 146A; towards the base, 144B to 144C; venation, similar to lamina. Fully expanded foliage, lower surface: 147B; towards the base, 147C to 147D; venation, 146B.

Flower description:

*Flower arrangement and shape.*—Small single star-shaped flowers arranged in terminal and axillary compound cymes; cymes roughly hemispherical. Flowers face mostly upright. Freely flowering, about 125 flowers and flower buds per lateral branch.

*Natural flowering season.*—Flowering continuous from August through September in The Netherlands.

*Flower longevity on the plant.*—Individual last about two weeks on the plant. Flowers persistent.

*Fragrance.*—Faint.

*Flower buds.*—Length: About 4 mm. Diameter: About 2.5 mm. Shape: Ovoid. Color: 145D; towards the apex, 153B to 153D; towards the base, 143B.

*Inflorescence diameter.*—About 14.3 cm.

*Inflorescence height.*—About 11.4 cm.

*Flowers.*—Diameter: About 8 mm. Depth (height): About 6 mm.

*Petals.*—Arrangement: Five, fused at base. Length: About 3 mm. Width: About 1.5 mm. Shape: Ovate. Apex: Acute. Margin: Entire. Texture, upper and lower surfaces: Smooth, glabrous. Color: When opening, upper and lower surfaces: 145C to 145D. Fully opened, upper and lower surfaces: Close to 3A.

*Calyx.*—Arrangement: Five sepals fused at the base; campanulate. Length: About 1 mm. Diameter: About 0.8 mm. Sepal shape: Narrowly ovate. Sepal apex: Acute. Sepal texture, upper and lower surfaces: Smooth, glabrous. Sepal color, upper and lower surfaces: 143A to 143B.

*Peduncles.*—Length: About 8.4 cm. Diameter: About 3 mm. Strength: Moderately strong. Texture: Smooth, glabrous. Aspect: Erect to about 25° from vertical. Color: 144B to 144C.

*Pedicels.*—Length: About 4 mm. Diameter: About 1 mm. Strength: Moderately strong. Texture: Smooth, glabrous. Aspect: Erect to about 45° from the stem axis. Color: 144B.

*Reproductive organs.*—Stamens: Quantity per flower/arrangement: About ten; five stamens at base of petals; other five, free. Anther shape: Broadly oblong; flattened. Anther length: About 0.5 mm. Anther color: 4B; towards the apex, 34B to 34C. Filament length: About 3.5 mm. Filament color: 157D. Pollen amount: Scarce. Pollen color: 8D. Pistils: Quantity/arrangement: Five per flower; prominent; fused at the base; star-shaped. Pistil length: About 3 mm. Stigma shape: Rounded; minute. Stigma color: 144C. Style length: About 2.5 mm. Style color: 145A to 145B. Ovary color: 145A to 145B.

*Seed/fruit.*—Seed and fruit production has not been observed.

Disease/pest resistance: Plants of the new *Sedum* have not been noted to be resistant to pathogens and pests common to *Sedum.*

Weather tolerance: Plants of the new *Sedum* have exhibited good tolerance to rain and wind and have been observed to tolerate temperatures from −10 to 35° C.

It is claimed:

1. A new and distinct cultivar of *Sedum* plant named 'Sunkissed', as illustrated and described.

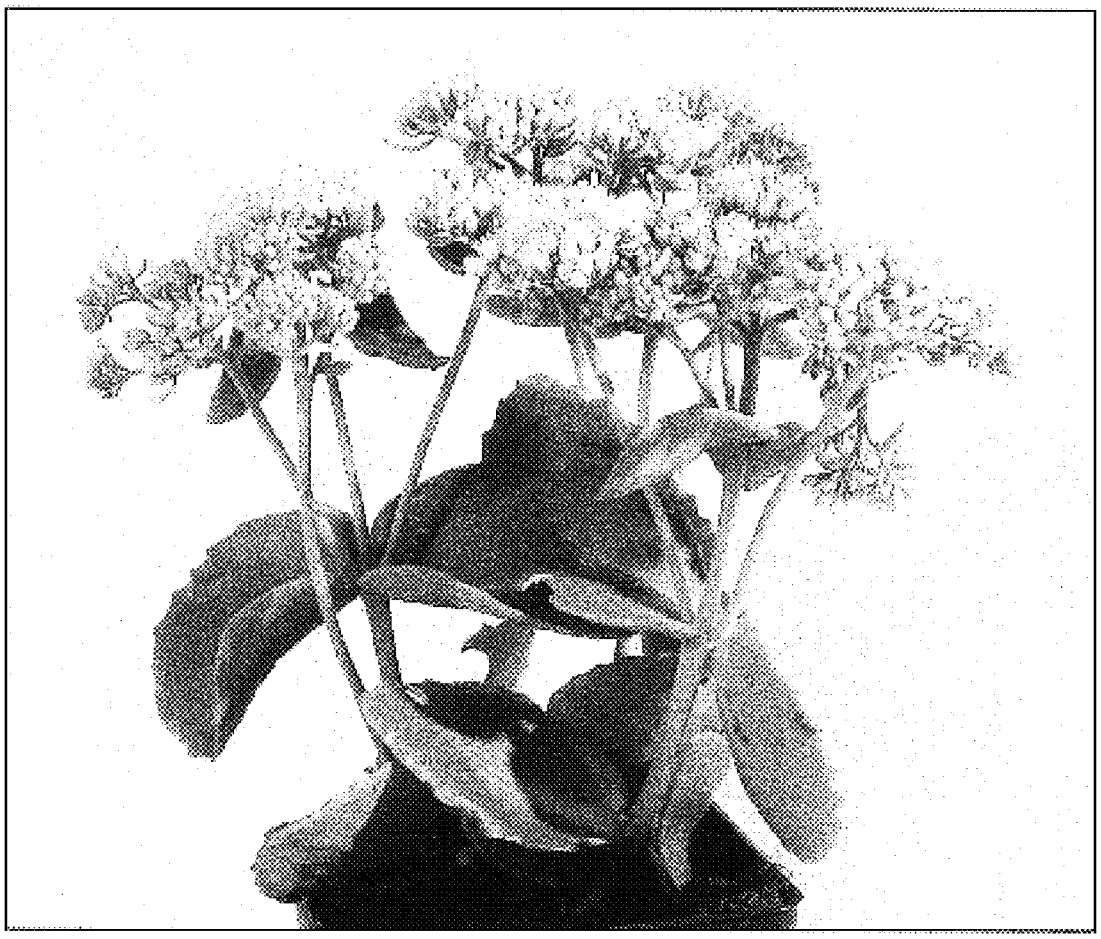

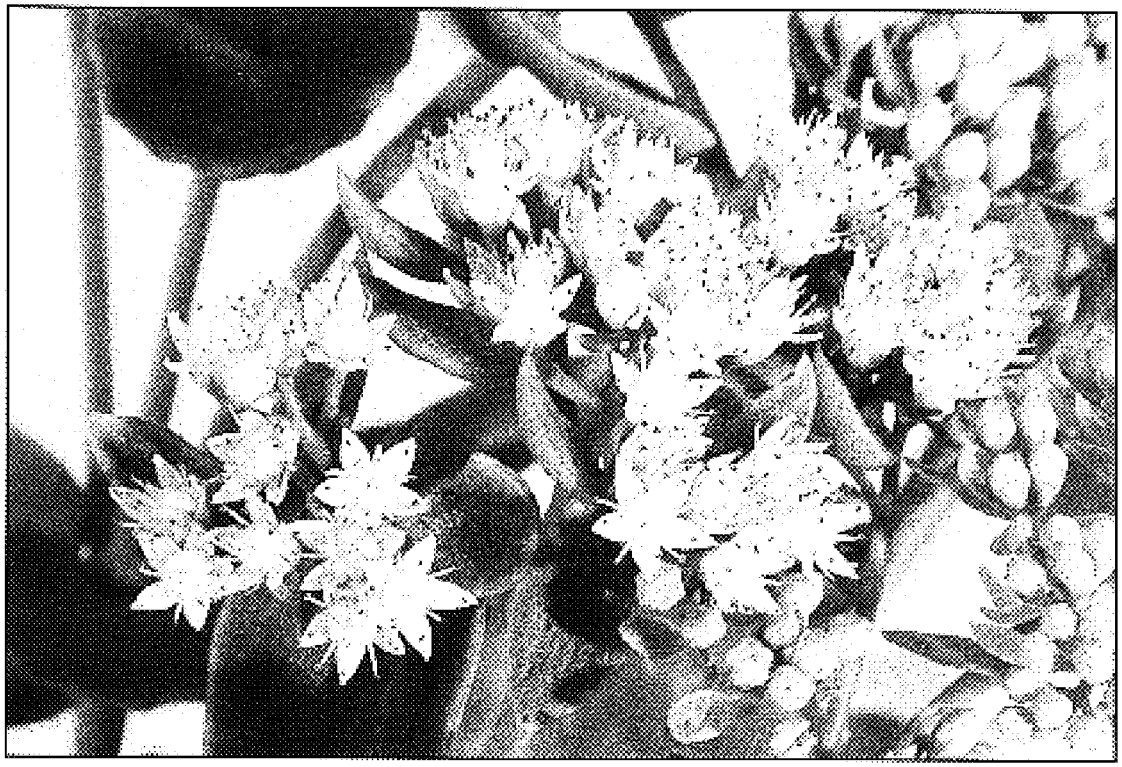
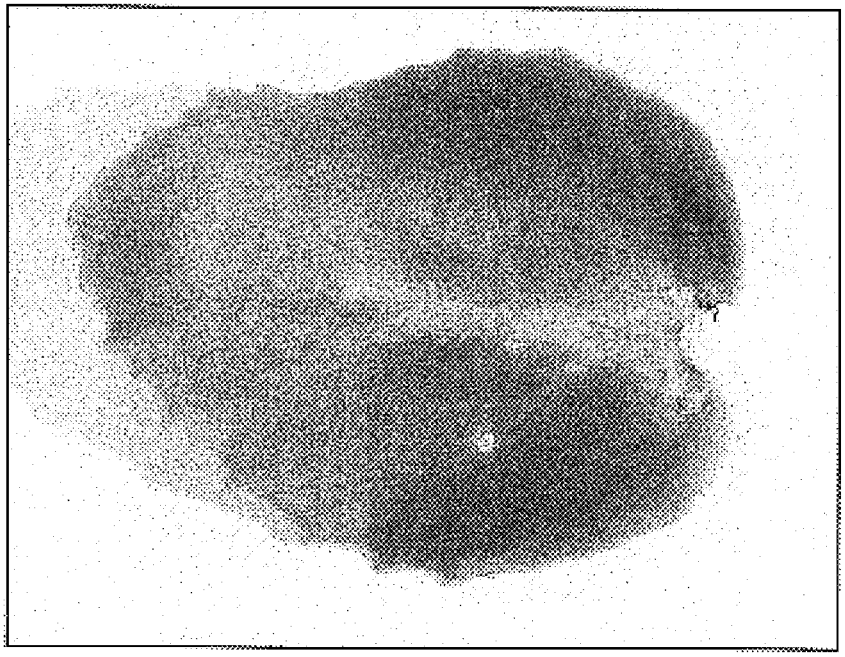

* * * * *